US00PP29551P3

(12) United States Plant Patent
Maillard et al.

(10) Patent No.: US PP29,551 P3
(45) Date of Patent: Jul. 31, 2018

(54) PEACH TREE NAMED 'CRISPREVE'

(50) Latin Name: ***Prunus persica* (L.) Batsch**
Varietal Denomination: CRISPREVE

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/330,877

(22) Filed: Nov. 10, 2016

(65) Prior Publication Data

US 2017/0156247 P1 Jun. 1, 2017

(30) Foreign Application Priority Data

Nov. 27, 2015 (QZ) ..... PBR 2015/2862

(51) Int. Cl.
*A01H 5/08* (2018.01)

(52) U.S. Cl.
USPC ..... Plt./197

(58) Field of Classification Search
USPC ..... Plt./194, 197, 198
See application file for complete search history.

*Primary Examiner* — Susan McCormick Ewoldt
(74) *Attorney, Agent, or Firm* — Westerman, Hattori, Daniels & Adrian, LLP

(57) ABSTRACT

A new and distinct variety of yellow peach tree denominated 'CRISPREVE' has a low chill requirement, fruits with high eating quality and very long shelf life without alteration before and after harvesting, with a semi-sweet orange yellow flesh, with a slightly red pigmentation into the stone cavity and along the pistillary conduct, and an attractive luminous and homogenous skin with a high percentage of purple red blush on skin surface, on an orange red background.

2 Drawing Sheets

Botanical classification: *Prunus persica* (L.) Batsch.

Variety denomination: 'CRISPREVE'.

This application claims priority of Community plant variety right No. 2015/2862 filed on Nov. 27, 2015 (Nov. 27, 2015) which is hereby incorporated by reference in its entirety.

BACKGROUND OF THE NEW VARIETY

The present invention relates to a new and distinct variety of yellow peach tree, *Prunus persica* (L.) Batsch, which has been given the variety denomination 'CRISPREVE'.

This new tree produces fruits with a long shelf life without alteration both on the tree after growth completion and after harvesting, very good eating quality, clingstone orange yellow flesh fruits with a very slightly red pigmentation, for fresh market in end of July in the Pyrénées-Orientales department, France.

ORIGIN OF THE VARIETY

The 'CRISPREVE' yellow peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CRISPREVE' variety resulted from a pollinated cross between the 'NECTARFLORA' white nectarine tree (U.S. Plant Pat. No. 22,504) which was used as the seed parent and a yellow peach tree unselected cultivar named 'ASF PJ BZ0104' (not patented) which was used as the pollen parent.

The 'CRISPREVE' variety was obtained by hybridizing and propagated by grafting on a "INRA® GF677" rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CRISPREVE' yellow peach tree blooms generally during the first two weeks of February near Elne in the Pyrénées-Orientales department, France. More particularly, the beginning of the blooming period occurs between January 30$^{th}$ and February 20$^{th}$. The blooming period is considered very early. However, it was observed that its early date of blooming seems to be highly dependant on climatic conditions.

The first fruit of 'CRISPREVE' ripens generally at the beginning or in the middle of July. More particularly, the beginning of the ripening period occurs between June 28$^{th}$ and July 16$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
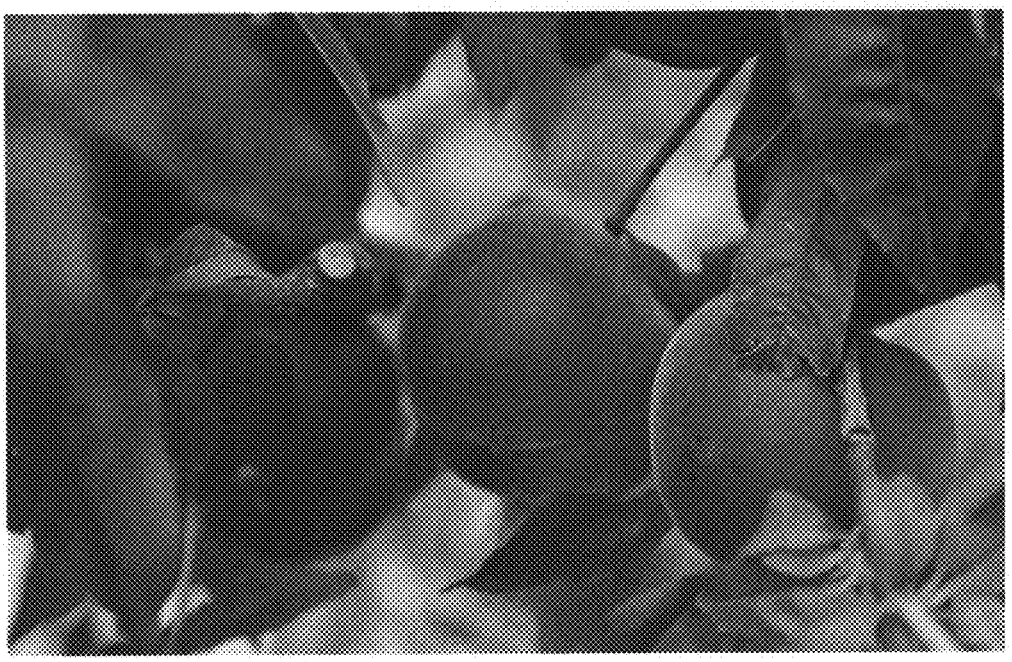
FIG. 1 is a color photograph that shows a close view of typical specimens of the fruit of the new variety 'CRISPREVE' on the tree.
Figure 2:
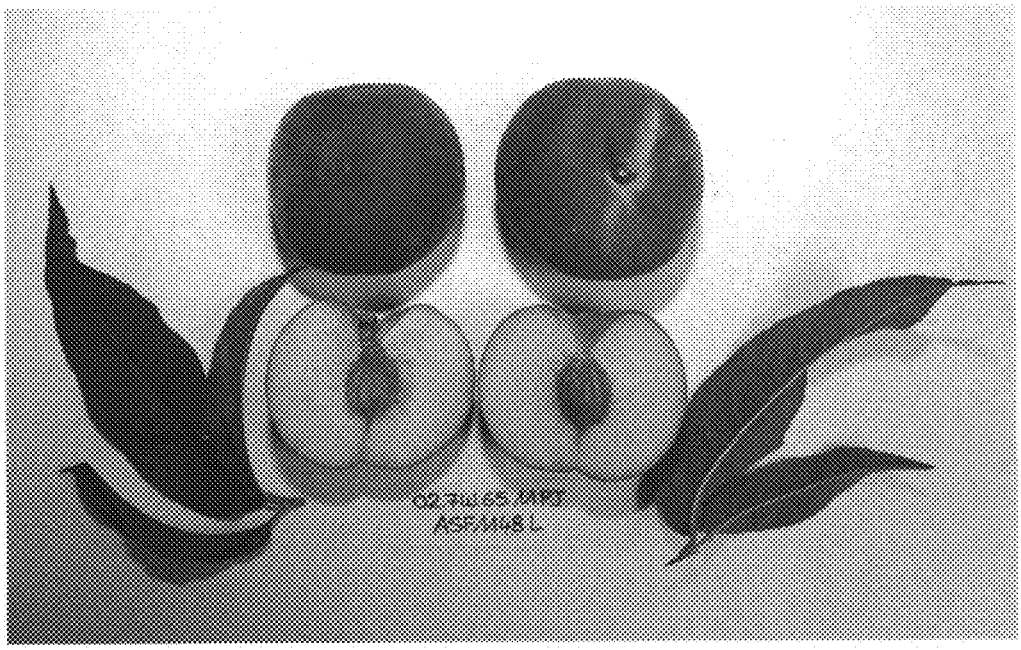
FIG. 2 is a color photograph which shows three typical specimens of the fruit, one having been cut in half with the pit being left in one of the halves for depicting leaves, fruit flesh, pit and pit cavity of the new variety
Figure 3:
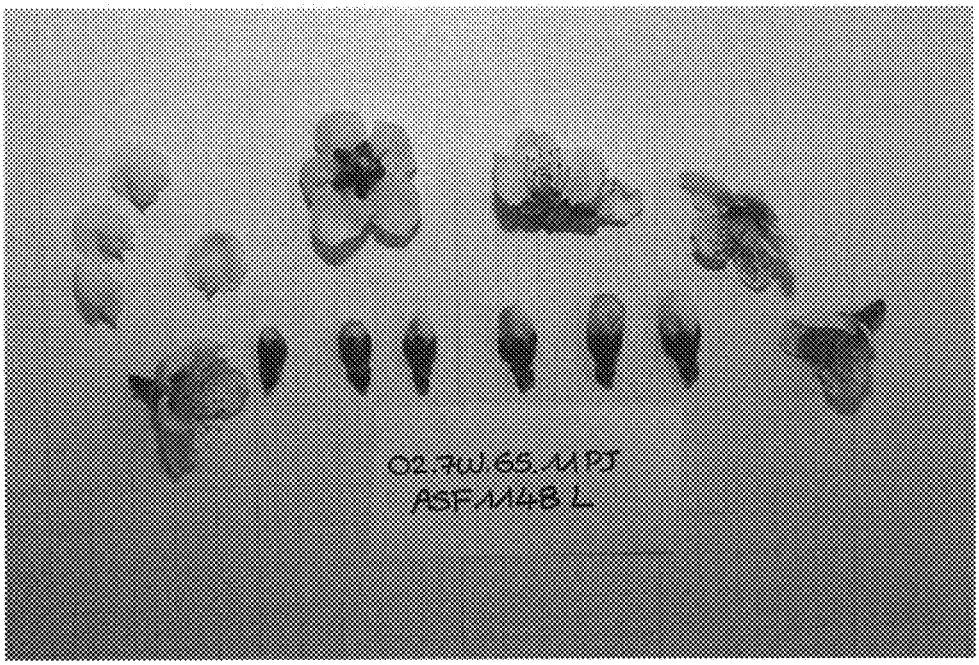
FIG. 3 is a color photograph which depicts the flower buds at different development stages, and the reverse and side view of the flower and the reproductive organs with petals removed, of the new variety.
Figure 4:
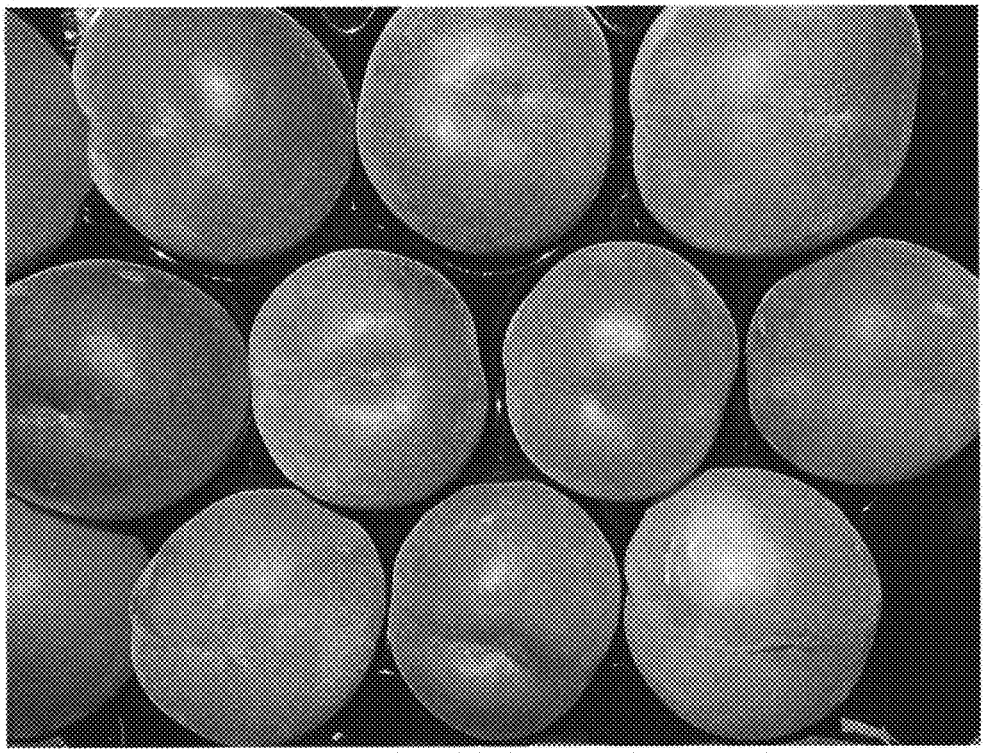
FIG. 4 is a color photograph that shows a close view of typical specimens of the fruit of the new variety 'CRISPREVE' at ripening time.

The enclosed photographs show plants in their third growing season.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CRISPREVE' is high, due to fruit very long shelf life without alteration after harvesting.

Trees are vigorous and large stature half-standing in a semi-flared to semi-upright out aspect. The anthocyanic coloration of flowering shoot is present excluding brushwood side away from sun. The time of beginning of flowering is considered very early; flowering begins at the beginning of February. The type of flower is showy with medium petal size. Petals are medium pink. Leaf glands are present and round. The fruit flesh orange yellow generally with a very slightly red pigmentation into the stone cavity and along the pistillary conduct. The fruit skin is thick, with a luminous and homogenous red purple blush on an orange red background. The stone is clingstone and its size is small for the variety. Fruit taste is semi-sweet, very aromatic and with a high level of sugars.

Compared to 'CRISPSTAR' variety (not patented), 'CRISPREVE' variety has a similar period of maturity. The chilling requirement for 'CRISPSTAR' is medium to high whereas the new variety 'CRISPREVE' has a low chilling requirement. The amount of flower produced by the new variety, i.e. 45 to 50 flowers per linear meter is higher than the amount of flower produced by CRISPSTAR, which is about 40 flowers per meter. The amount of fruits produced by 'CRISPREVE' is also much more important (60T/HA) in comparison with the amount of fruits produced by 'CRISPSTAR'.

Compared to its pollen parent, a yellow peach tree unselected cultivar named 'ASF PJ BZ0104' (not patented) which has an early period of maturity, the fruits of the 'CRISPREVE' variety ripen later. Moreover, the taste of the pollen parent 'ASF PJ BZ0104' is balanced whereas the fruit flesh taste of the 'CRISPREVE' variety is semi-sweet.

DETAILED DESCRIPTION

Referring more specifically to the pomological details of this new and distinct variety of yellow peach tree, the following was observed on trees in their fifth growing season (fourth year of production), excepted for the observations made on trees, trunk and branches, which were performed on trees in their third growing season (second year of production). The characteristics were observed under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. (Royal Horticultural Society) Colour Chart (Fourth Edition) provided by The Royal Horticultural Society of Great Britain.

TREE

Size:

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduces to 250 cm the next years.

Spread: Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

Vigor: Considered strong.

Productivity: Very Productive and regular, every year. Fruit set is spaced by thinning to develop the remaining fruit into the desired market sized fruit. The number of the fruit set varies with the prevailing climatic conditions and cultural practices employed during the bloom period, and is therefore not distinctive of the present variety.

Bearer: Very regular. The fruit distribution is considered homogenous on mixed branches and spurs having more than 1 year. Thinning should be reduced or very reduced because of the capacity of the tree to produce homogeneous fruits with a high potential.

Form: The 'CRISPREVE' variety has naturally a semi-flared to semi-upright shape.

Density: Considered dense.

Hardiness: The present tree was grown and evaluated in France. The variety appears to be hardy under the central Pyrénées-Orientales departement typical climatic conditions. Experimentations on the same orchard in Elne, Pyrénées-Orientales department, with winter chilling requirement below 7.2° C. comprised between 350 hours and 1200 hours according to the specificities of the year, namely 1076 hours in 2012-2013, 767 hours in 2013-2014, 552 hours in 2014-2015, 721 hours in 2015-2016, and 784 hours in 2016-2017 showed a good behavior of the tree in all cases. No damages were caused by ascertained temperatures as low as −12 degrees Celsius in winter. The tree was also very resistant to frosty springtime weather.

TRUNK

Diameter: Approximately 6.9 centimeters in diameter when measured at a distance of approximately 20 centimeters above the soil level.

Bark texture: Considered rough, with lenticels.

Lenticels: Numerous lenticels are present. The number of lenticels reaches 2 lenticels per $cm^2$. The lenticels range in size from approximately 3.0 millimeters in width, and about 2.0 millimeters in height.

Lenticel color: The lenticels have a silver-grey color (RHS Grey 201 D).

Bark coloration: The bark has a silver color (RHS Grey 201 B to RHS Grey 201 C) slightly darker than the lenticel color.

BRANCHES

Size: Mature branches and current season shoots are considered medium to large for the variety.

Diameter: Average as compared to other peach varieties. The current season shoots have a diameter of about 3.0 millimeters, and mature branches have a diameter of about 6.0 millimeters.

Surface texture: Smooth for both current season shoots and mature branches, wood which is several years old has no furrowed appearance.

Crotch angles: Primary branches are considered variable, but the crotch angles are generally of 70 degrees from the horizontal axis. This particular characteristic is not considered distinctive of the variety, however.

Current season shoots:

Internode length: Generally between 22.0 and 25.0 millimeters.

Color of mature branches: Light brown (RHS Grey Brown 199 A to RHS Grey Brown 199 B).

Current seasons shoots:

*Color.*—The color of new shoot tips is considered light green (RHS Yellow Green 145 A) on lower part of new shoot tips, whereas the upper part is darker and colored in brown to purple red (RHS Greyed Purple 183 A to RHS Greyed Purple 183 B), depending on the level on the tip.

LEAVES

Size: Considered medium for the species. The ratio leaf length/leaf width is 3.74. This ratio is calculated with the medium length of five measures taken on five different leaves (158.6), divided by the medium width of also five measures (42.4).

Leaf arrangement: Alternate.

Leaf length: Approximately 152.0 to 165.0 millimeters with leaf petiole. The medium length is about 158.6 millimeters.

Leaf width: Approximately 42.0 to 43.0 millimeters. The medium width is 42.4 millimeters.

Leaf base shape: Concave.

Leaf form: Lanceolate.

Leaf tip form: Short, pointed and acuminate.

Leaf color:

*Upper leaf surface.*—Green (RHS Green 137 A).

*Lower surface.*—A lighter green (RHS Yellow Green 146 A) than the upper leaf surface color.

Leaf texture: Both surfaces of the leaves are smooth and glabrous.

Leaf venation: Pinnately veined.

Mid-vein:

*Color.*—Light green, almost cream white (RHS Yellow Green 145 D). The color may evolve with maturity.

Leaf margins: Slightly undulating.

Form: Considered slightly dentate.

Uniformity: Leaves are isolated or grouped by 2 or 3. In this last case, one leaf of normal size is found with one or two smaller leaves (at least 50% smaller).

Leaf petioles:

*Size.*—Considered medium to small.

*Length.*—About 8.0 to about 10.0 millimeters.

*Diameter.*—About 1.7 millimeters.

Petioles color:

*Upper petiole surface.*—Light green (RHS Yellow Green 144 A to RHS Yellow Green 144 B).

*Lower surface.*—Light green (RHS Yellow Green 144 C to RHS Yellow Green 144 D).

Leaf glands:

*Size.*—Considered small. Their size is about 0.7 millimeter in length and in width.

*Number.*—Generally 2 glands per leaf.

*Type.*—Round.

*Color.*—On young leaves, leaf glands color is considered a light green (RHS Green 145 B). On older leaves, leaf glands color turns to a dark brown (RHS Grey Brown 199 A to RHS Grey Brown 199 B).

*Margins.*—Smooth and regular.

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are round and balloon shaped. Their form is evolving until blooming, with variables dimensions. Just before blooming, floral buds are approximately 12.0 millimeters wide and approximately 18.0 millimeters long.

*Color.*—This characteristic is dependent upon the proximity to bloom. At pre-floral stage of development (stage A), the bottom of the flowers buds, formed by the sepals, is of purple-brown color (RHS Greyed Purple 183 A or RHS Greyed Purple 183 B or RHS Greyed Purple 183 C or RHS Greyed Purple 187 B or RHS Grey Brown Group 199 A near the base). The corolla, formed by the petals, is generally of medium pink color (RHS Red Purple 73 C or RHS Red Purple 73 D). Petals color shows an evolution until the end of flowering.

Hardiness: The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: The blooming time generally begins during the first two weeks of February. The first bloom was observed on 2011.

Blooming time: Considered very early in relative comparison to other commercial peach cultivars grown in the Pyrénées-Orientales departement, France. The date of full bloom is observed generally at the middle of the blooming period. The date of bloom varies slightly with climatic conditions and cultural practices. Thus the full bloom was observed from February 15$^{th}$ until Feb. 26, 2011, then from February 22$^{th}$ until Mar. 4, 2012, then from January 30$^{th}$ until Feb. 16, 2013, then from February 4$^{th}$ until Feb. 14, 2014 and from February, 20$^{th}$ until Feb. 28, 2015.

Duration of bloom: Approximately 9 to 18 days. This characteristic varies slightly with the prevailing climatic conditions.

Flower type: The variety is considered to have a showy type flower.

Flower size: Considered medium. Flower diameter at full bloom is approximately 30.0 to 35.0 millimeters.

Bloom quantity: Considered very abundant, approximately between 45 and 50 flowers per meter, with a good distribution and a high rate of fruit set.

Flower bud frequency: Generally 2 flower buds appear per node, occasionally 1.

Petal size:

*Generally.*—Considered medium.

Length: Generally 17.0 to 18.0 millimeters.

Width: Generally 15.0 to 17.0 millimeters.

Petal form: Round-shaped.

Petal count: Generally 5.

Petal texture: Both surfaces of the petals are smooth, glabrous and soft.

Petal color: Both surfaces of the petal are colored with a medium pink (RHS Red Purple 73 C or RHS Red Purple 73 D) when young, becoming slightly darker until the end of blooming.

Petal arrangement: Overlapping.

Fragrance: Sweet.

Petal claw:

*Form.*—The claw is considered to have a triangular form, narrower at the base.

*Color.*—RHS Red Purple 73 B.

Petal margins: Generally considered moderately wavy, sinuate.

Petal apex:

*Generally.*—The petal apices are generally round.

Flower pedicel:

*Length.*—Considered medium and having an average length of approximately 3.0 millimeters.

*Diameter.*—Considered average, approximately 2.0 millimeters.

*Color.*—Yellow Green (RHS Yellow Green N144 A or RHS Yellow Green N144 B).

Calyx:

*Internal surface texture.*—Smooth and glabrous.

*Color.*—At the stage F of blooming, when the flower is open, the inner surface of the calyx is matt and considered golden-orange (RHS Greyed Red 178 C to RHS Greyed Red 178 D). The outer surface of the calyx is considered of purple-brown color (RHS Greyed Purple 183 A to RHS Greyed Purple 183 B to RHS Greyed Purple 183 C or RHS Greyed Purple 187 B and RHS Yellow Green 144 A to RHS Yellow Green 144 B at the base).

Sepals:

*Surface texture.*—The outer surface has a fine pubescent texture.

*Size.*—Medium.

*Form.*—Conic with a round tip.

*Length.*—Approximately 5.0 millimeters.

*Width.*—Approximately 5.0 millimeters.

*Color.*—At the stage F of blooming, the outer surface of the sepals is considered of purple-brown color (RHS Greyed Purple 183 A to RHS Greyed Purple 183 B to RHS Greyed Purple 183 C or RHS Greyed Purple 187 B and RHS Yellow Green 144 A to RHS Yellow Green 144 B at the base). The inner surface of the sepals is matt and considered golden-orange (RHS Greyed Red 178 C to RHS Greyed Red 178 D).

Average number of stamens per flower: Approximately 43 to 50 stamens per flower.

Anthers:

*Color.*—At an early stage of maturity, anthers are colored with an orange yellow color (RHS Yellow Orange 16 A to RHS Yellow Orange 16 B). The color may evolve with maturity to turn in a red or red orange color (RHS Red Group N34 A or RHS Greyed Red Group 178 A).

Pollen production: Pollen is abundant, and has a yellow color (Approximately RHS Yellow Orange 17 B to RHS Yellow Orange 17 C) which may evolve with maturity. The present variety is considered auto-fertile (self-pollinating).

Filaments:

*Size.*—Medium length, between 9.0 and 16.0 millimeters in length. Filaments length is generally higher than the pistil's length, or equal to the pistil's length.

Color: Considered white (RHS White N 155 D) to pale pink (RHS Red Purple 62 D). The color becomes darker during the blooming.

Pistil:

*Number.*—Usually 1.

*Generally.*—Average in size.

*Length.*—Approximately 16.0 to 18.0 millimeters including the ovary.

*Color.*—Considered a very pale green (RHS Yellow Green Group 151 D). The color evolves during the blooming, becoming more light (RHS Yellow Green Group 150 D) and sometimes very slightly pink (RHS Red Group 36D) at the end of the blooming.

Ovary:

*Pubescence.*—Present.

FRUIT

Maturity when described: Firm in ripe conditions (shipping ripe).

Date of first picking: Jul. 1, 2011.

Date of last picking: The date of harvest varies slightly with the prevailing climatic conditions. The 'CRISPREVE' variety has a medium date of picking, and a grouped maturity. The maturity is grouped within 5 to 11 days and the harvest is generally performed in two runs. Last known picking times carry on July 1$^{st}$ to Jul. 7, 2011, then on July 14$^{th}$ to Jul. 18, 2012, then on July 16$^{th}$ to Jul. 24, 2013, then on June 28th to Jul. 6, 2014 and finally on July 8$^{th}$ to Jul. 18, 2015.

Size:

*Generally.*—Homogeneous in size. Considered large.

*Form.*—Round to slightly flattened.

Average cheek diameter: Approximately 64.0 to 67.0 millimeters.

Average axial diameter: Approximately 54.0 to 58.0 millimeters.

Typical weight: Generally about 135.0 to 160.0 grams. This characteristic is high dependent upon the prevailing cultural practices, and therefore is not particularly distinctive of the variety.

Fruit form:

*Generally.*—Round. The fruit is generally uniform in symmetry, viewed from the suture's plane.

Suture:

Fruit suture: Wide-mouthed and slightly marked, extending from the base to the apex. No apparent callousing or stitching exists along the suture line. Not pointed.

*Color.*—The suture has generally a similar color to the whole fruit color, a luminous purple red (RHS Greyed Purple 187 A).

Ventral surface:

*Form.*—Smooth.

Apex: Non-prominent, small and generally slightly depressed.

Base: Semi-flared, shallow.

Stem cavity: Average depth of the stem cavity is about 15.0 millimeters. Average width is about 22.0 millimeters.

Fruit skin:

*Thickness.*—Considered thick and strong, and the adherence of skin to flesh is strong to medium, depending on the fruit maturity.

*Texture.*—Fine pubescence.

*Taste.*—Semi-sweet.

*Tendency to crack.*—None observed.

Color:

*Blush color.*—This blush color is an homogenous purple red (RHS Greyed Purple 187 A). The purple red blush covers approximately 75% of the fruit skin surface on an orange red background (RHS Orange Red N 34 A) on approximately 25% of the fruit skin surface. The percentage of the blush on the fruit skin surface can vary, and is generally dependant upon the prevailing conditions under which the fruit was grown.

*Ground color.*—The ground color covers approximately 25% of the fruit skin surface, and is considered orange red (RHS Orange Red N 34 A).

Fruit stem: Medium in length, approximately 10.0 to 11.0 millimeters.

Diameter: Approximately 4.0 to 5.0 millimeters.

Color: Pale green (RHS Yellow Green 145 A to RHS Yellow Green 145 B).

Flesh:

*Ripens.*—Very homogenously, slowly. The flesh has a long shelf life.

*Texture.*—Very firm, very dense, crunchy, melting, juicy at harvest maturity stage.

*Fibers.*—Not fibrous.

*Aroma.*—Pronounced.

*Eating quality.*—Considered very good, aromatic, with a high level of sugars but semi-sweet due to acidity level between 6 and 9 meq/100 mL.

*Flavor.*—Considered semi-sweet. The Brix is generally between 13 and 15.

*Juice.*—Very juicy at complete maturity.

*Brix.*—Generally 13.0 to 15.0 degrees. This characteristic varies slightly with the number of fruit per tree; prevailing cultural practices; and the surrounding climatic conditions.

*Flesh color.*—Orange yellow flesh (RHS Yellow Orange 15 A to RHS Yellow Orange 15 B) usually with a very slightly red pigmentation (RHS Orange Red N34 A) into the stone cavity and along the pistillary conduct.

STONE

Type: Clingstone, more or less adherent depending on the fruit maturity.

Size: Considered small for the variety. The stone size varies significantly depending upon the tree vigor, crop load and prevailing growing conditions.

Length: Approximately 22.0 to 23.0 millimeters.

Width: Approximately 18.0 to 19.0 millimeters.

Diameter: Approximately 15.0 to 16.0 millimeters.

Form: Elliptic.

Base: Straight to round.

Apex:

*Shape.*—The stone apex is short and pointed.

Stone cavity: Considered small size, with an ovate-form and dimensions corresponding to the stone's dimensions.

Stone surface:

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small, and having a depth of approximately 1.0 millimeters at mid-suture.

Dorsal edge:

*Shape.*—Grooved.

Stone color: The color of the dry stone is generally considered light orange brown (RHS Greyed Orange 164 B to RHS Greyed Orange 164 C).

Tendency to split: Splitting is very low or absent, depending on climatic conditions between blooming period and stone hardening.

Kernel:

*Size.*—The kernel is considered small.

*Length.*—Approximately 13.0 millimeters.

*Width.*—Approximately 8.0 millimeters.

*Thickness.*—Approximately 4.0 millimeters.

*Form.*—Considered flattened and elliptic.

*Pellicle.*—The pellicle of the kernel has a short pubescence.

*Color.*—The kernel skin is light orange-brown colored (RHS Greyed Orange N 167 A). The almond, which is the seed of the kernel, is cream white (RHS White 155 B) and has a bitter tasting. The kernel and its embryo are mature at the time of fruit maturity.

Use: The subject variety 'CRISPREVE' is considered to be a yellow peach tree of the medium season of maturity, and which produces fruits that are considered firm, attractively colored with a luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

Keeping quality: Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

Shipping quality: Considered very good. The fruit of the new yellow peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

Resistance to insects and disease: No particular susceptibilities were noted. The present variety is not very sensitive to powdery mildew, or conservation diseases and decay due to its thick and strong skin.

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of yellow peach tree as illustrated and described, characterized by its low chill requirement, fruits with high eating quality and very long shelf life without alteration before and after harvesting, with a semi-sweet orange yellow flesh, with a slightly red pigmentation into the stone cavity and along the pistillary conduct, and an attractive luminous and homogenous skin with a high percentage of purple red blush on skin surface, on an orange red background.

* * * * *